United States Patent [19]

Rajagopalan

[11] 4,351,836
[45] Sep. 28, 1982

[54] 1,2,3,4,4A,5,10,10A-OCTAHYDRO-5,10-ORTHO-BENZENOBENZ[G]ISOQUINO-LINES AND ANTIDEPRESSANT USE THEREOF

[75] Inventor: Parthasarathi Rajagopalan, Wilmington, Del.

[73] Assignee: E. I. Du Pont de Nemours and Company, Wilmington, Del.

[21] Appl. No.: 172,991

[22] Filed: Jul. 28, 1980

[51] Int. Cl.$^3$ .................... A61K 31/47; C07D 221/22
[52] U.S. Cl. ...................................... 424/258; 546/58
[58] Field of Search ........................... 546/58; 424/258

[56] References Cited

U.S. PATENT DOCUMENTS 3,123,618  3/1964  Schumann et al. ................. 260/313

FOREIGN PATENT DOCUMENTS 2802159  1/1978  Fed. Rep. of Germany ...... 546/101

OTHER PUBLICATIONS

Chemical Abstracts 92:110819f.

Primary Examiner—David B. Springer

[57] ABSTRACT

This invention relates to (±)1,2,3,4,4a,5,10,10a-octahydro-5,10-o-benzenobenz[g]isoquinoline derivatives which are useful as antidepressants.

12 Claims, No Drawings

1,2,3,4,4A,5,10,10A-OCTAHYDRO-5,10-ORTHO-BENZENOBENZ[G]ISOQUINOLINES AND ANTIDEPRESSANT USE THEREOF

BACKGROUND OF THE INVENTION

This invention relates to novel benzenobenzisoquinoline derivatives, pharmaceutical compositions containing the novel compounds and methods of using the novel compounds to alleviate depression in mammals.

Mental illnesses include psychoses and neuroses. The symptoms requiring treatment include depression, anxiety, agitation and hallucinations. Drugs used particularly for treatment of both reactive and endogenous depressions include monoamine oxidase (MAO) inhibitors such as iproniazid, tranylcypromine, nialamide, phenelzine and pargyline and the non-MAO inhibition tricyclic aromatic dibenzazepines such as imipramine and dibenzocycloheptadienes such as amitriptyline.

All of these drugs have side effects that limit their usefulness. The MAO inhibitors may cause tremors, insomnia, hyperhydrosis, agitation, hypermanic behavior, confusion, hallucinations, convulsions, orthostatic hypertension and death. They frequently cause dizziness, vertigo, headache, inhibition of ejaculation, difficulty in urination, weakness, fatigue, dry mouth, constipation and blurred vision. Imipramine may cause blurred vision, dryness of mouth, constipation, urinary retention, orthostatic hypotension, respiration depression, myocardial infarction and congestive heart failure. Similar difficulties are experienced with amitriptyline.

There is a genuine need for psychotherapeutic agents which are effective and have fewer side effects than the drugs in use today. There is also need for drugs which have different modes of action than those presently used since none of the known drugs is completely effective.

SUMMARY OF THE INVENTION

It has now been found that compounds of Formula I satisfy these criteria.

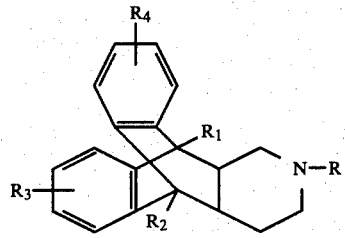

I where
R is H; $C_1$-$C_6$ alkyl, optionally substituted with —$OR_5$, phenyl or 1-adamantyl;

—$(CH_2)_n\overset{O}{\overset{\|}{C}}R_6$; —$(CH_2)_m\overset{O}{\overset{\|}{C}}OR_7$; or

—$CH_2CH(C_6H_5)_2$;

$R_1$ and $R_2$ are both H, or, when R=H or $CH_3$, one of $R_1$ and $R_2$ may be $CH_3$;
$R_3$ and $R_4$ are independently H, Cl, F or $CH_3$;
$R_5$ is H, $CH_3$ or phenyl;
$R_6$ is $C_1$-$C_3$ alkyl;
$R_7$ is H or $C_1$-$C_4$ alkyl;

n is 1, 2, 3 or 4; and
m is 0, 1, 2, 3 or 4;
provided that, when m=0, then $R_7$ is other than H; and pharmaceutically suitable acid and base salts thereof.

Preferred for reasons of superior activity are those compounds of Formula I where, independently,
R is H, $CH_3$ or —$CO_2CH_2CH_3$; or
$R_1$ and $R_2$ are H; or
$R_3$ and $R_4$ are H or mono-F.

More preferred for the same reasons are those preferred compounds where
R, $R_3$ and $R_4$ are H.

The following compounds are specifically preferred by reason of their outstanding activity:
(±)1,2,3,4,4a,5,10,10a-octahydro-5,10-o-benzobenz[g]isoquinoline hydrochloride;
(±)7-fluoro-1,2,3,4,4a,5,10,10a-octrahydro-5,10-o-benzobenz[g]isoquinoline hydrochloride;
(±)8-fluoro-1,2,3,4,4a,5,10,10a-*octahydro*-5,10-o-benzobenz[g]isoquinoline hydrochloride; and
(±)1,2,3,4,4a,5,10,10a-octahydro-5,10-o-benzobenz[g]isoquinoline-2-carboxylic acid, ethyl ester.

Pharmaceutically suitable acid and base salts of the compounds of Formula I are made with physiologically acceptable acids and bases which are known in the art. Such acid salts include hydrochloride, sulfate, phosphate, nitrate, citrate and maleate; base salts, when R=—$(CH_2)_mCO_2H$, include sodium, potassium, and ammonium.

DETAILED DESCRIPTION OF THE INVENTION

A number of routes are available for synthesizing the compounds of Formula I (hereinafter called the compounds of this invention). The two compounds wherein R=$COOC_2H_5$ (Ia) and R=H (Ib) are useful starting materials for preparing other compounds of this invention and may be prepared as follows:

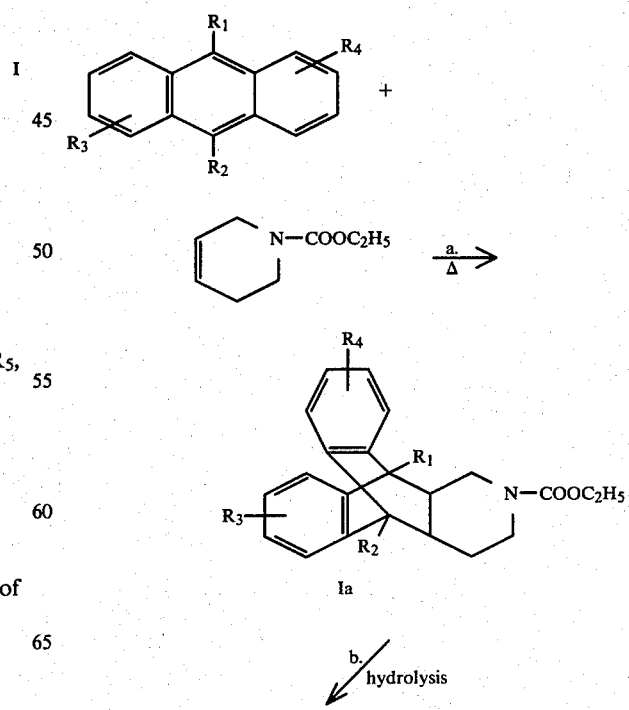

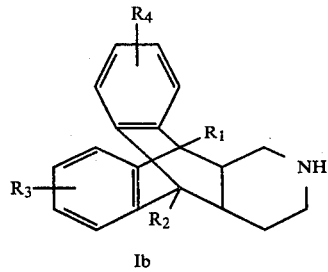

Ib

In step a, a mixture of a properly substituted anthracene and 1-ethoxycarbonyl-1,2,5,6-tetrahydropyridine is heated at temperatures of about 180° C. to about 220° C. for approximately 12 to 24 hours. This may be done with or without solvents and either under pressure or in an inert atmosphere. In step b, the 2-carboxylic acid ethyl ester compound of Formula Ia is hydrolyzed to the compound of Formula Ib by heating the former with alkali (for example, sodium or potassium hydroxide) in a solvent at the boiling point of the solvent. Suitable solvents include alcohols, for example, ethanol, 2-propanol and 1-butanol. The reaction is usually completed after heating for a period of about two to six hours.

Compounds Ia and Ib can be used to prepare other compounds of Formula I.

Route 1

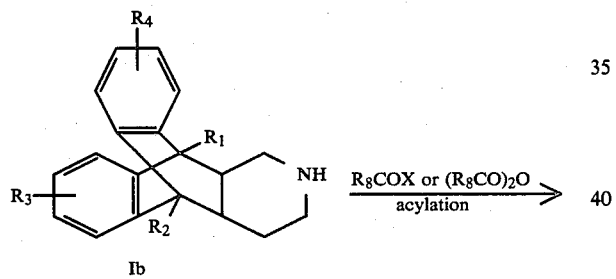

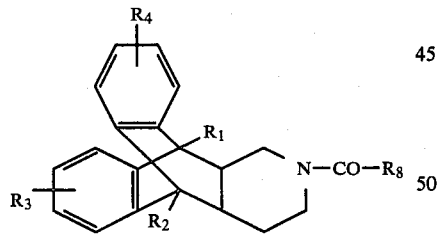

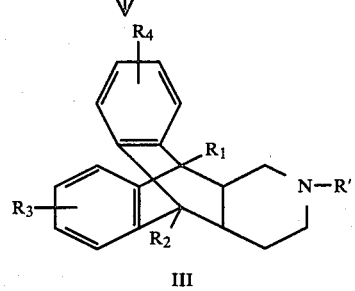

where $R_8 = C_1-C_5$ alkyl, optionally substituted with $OR_5$, phenyl, adamantyl or $-CH(C_6H_5)_2$.

In the first step of Route 1, a compound of Formula Ib is contacted, in the presence of a base, with an acid halide of the type $R_8COX$, where X is halogen, or an anhydride of the type $(R_8CO)_2O$. Either organic bases, for example triethylamine, or inorganic bases, for example sodium or potassium carbonate, are suitable. Any inert solvent may be used; chloroform, methylene chloride and tetrahydrofuran are examples of suitable solvents. Temperature and pressure are not critical.

In step b of Route 1, a compound of Formula II is reduced to yield a compound of Formula III. Suitable reducing agents include diborane or borane-dimethyl sulfide complexes and metal hydrides such as lithium aluminum hydride or sodium dihydrobis(2-methoxyethanolato)aluminate. The solvent used will depend on the reducing agent used; a suitable solvent for use with the diborane or borane complexes is tetrahydrofuran and suitable solvents for use with the metal hydrides are tetrahydrofuran or benzene. The compound of Formula II and the reducing agent are preferably treated together at the boiling point of the solvent for a period of about one to six hours.

Route 1 can be used to prepare any of the compounds of this invention with the exception of those where $R = H$ or

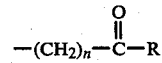

or

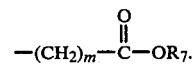

Thus, R' in Formula III can be $C_1-C_6$ alkyl optionally substituted with $-OR_5$, phenyl or adamantyl; or $-CH_2CH(C_6H_5)_2$. The definition of $R_8$ will, of course, depend on the desired product of Formula III. For example, when a compound of Formula III where $R^1$ is $-CH_2CH_2OCH_3$ is desired, $R_8$ would be $CH_2OCH_3$.

Route 2

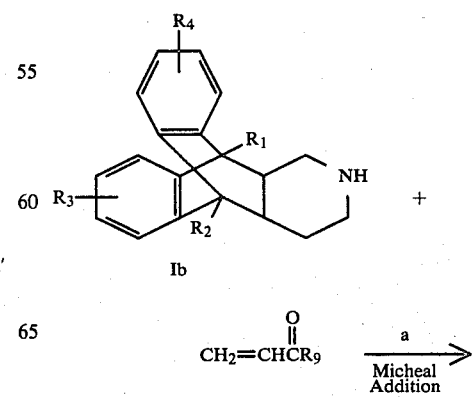

-continued
Route 2

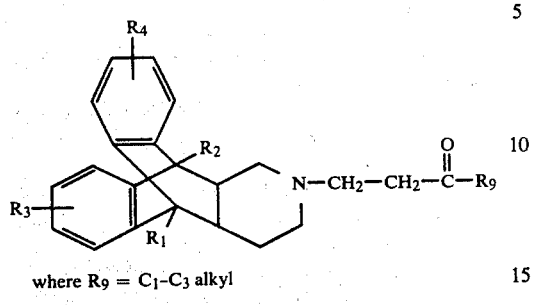

where R$_9$ = C$_1$-C$_3$ alkyl

IV b. reduction

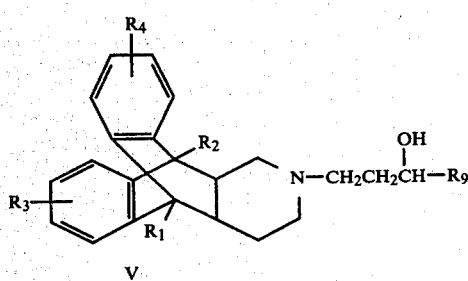

V

In step a of Route 2, an α,β-unsaturated carbonyl compound of the formula CH$_2$=CHCOR$_9$ (R$_9$=C$_1$-C$_3$ alkyl) is added to a compound of Formula Ib. The compounds are contacted in a suitable solvent, for example ethanol, and are preferably heated at the boiling point of the solvent for a period of about two to six hours.

In step b of route 2, a compound of Formula IV produced via step a is contacted with a reducing agent to yield a compound of Formula V. Suitable reducing agents include diborane, borane-dimethyl sulfide complex, metal hydrides, for example lithium aluminum hydride and sodium borohydride. The reactants are preferably heated at the boiling point of the solvent for a period of about one to six hours.

Route 3

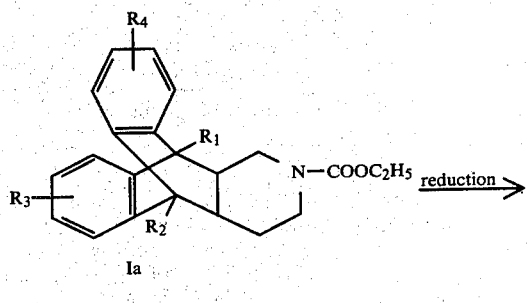

Ia

-continued
Route 3

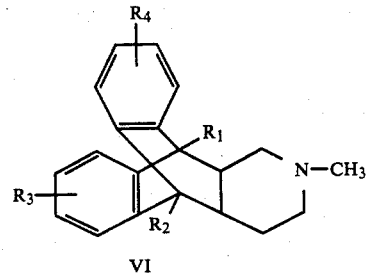

VI

Compounds of this invention in which R=CH$_3$, represented above by Formula VI, can be prepared by reduction of urethanes of Formula Ia. Suitable reducing agents include metal hydrides, for example, lithium aluminum hydride in tetrahydrofuran and sodium bis(2-methoxyethanolato)aluminate in benzene. The reactants are preferably heated for a period of about two to six hours at the boiling point of the solvent.

Route 4

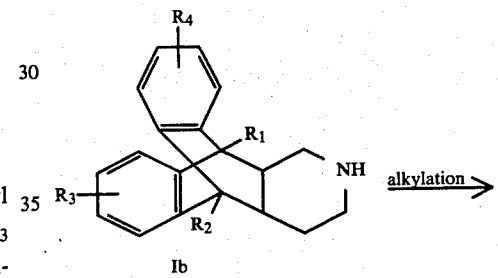

Ib alkylation →

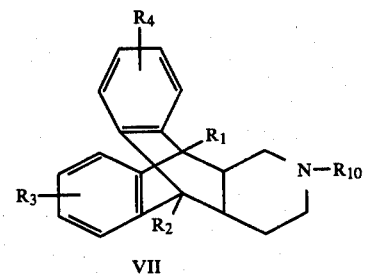

VII where
R$_{10}$ = C$_1$-C$_6$ alkyl;
—(CH$_2$)$_n$COR$_6$; or
—(CH$_2$)$_m$COOR$_7$.

The synthesis illustrated above as Route 4 may be used to prepare the compounds of this invention in which R=C$_1$-C$_6$ alkyl, —(CH$_2$)$_n$COR$_6$ or —(CH$_2$)$_m$COOR$_7$. A compound of Formula Ib is contacted with an alkyl halide in the presence of either an organic or an inorganic base, for example triethylamine or potassium carbonate. Polar solvents such as ethanol or dimethylformamide are preferred. The reactants are preferably heated at temperatures of about 70° to 100° C. for a period of about four to twenty-four hours.

The preparation of the compounds of this invention is illustrated by the following examples in which all temperatures are in degrees centigrade.

EXAMPLE 1

(±)1,2,3,4,4a,5,10,10a-Octahydro-5,10-o-benzenobenz[g]isoquinoline-2-carboxylic Acid, Ethyl Ester A mixture of 100 g of anthracene and 350 ml of 1-ethoxycarbonyl-1,2,5,6-tetrahydropyridine was stirred and refluxed for 20 hours in an atmosphere of nitrogen. Excess of the tetrahydropyridine was then removed under reduced pressure and the residue was cooled to 60° and triturated with ethanol. The product was filtered off and recrystallized from ethanol to yield the title compound, m.p. 170°–173°.

EXAMPLE 2

(±)1,2,3,4,4a,5,10,10a-Octrahydro-2-methyl-5,10-o-benzenobenz[g]isoquinoline Hydrochloride A 70% benzene solution of sodium dihydrobis(2-methoxyethanolato)aluminate (80 g) was added dropwise to a stirred solution of (±)-1,2,3,4,4a,5,10,10a-octahydro-5,10-o-benzenobenz[g]isoquinoline-2-carboxylic acid ethyl ester (8.0 g) in anhydrous benzene (100 ml). After the addition was complete, the mixture was stirred and refluxed for 2 hours, protected from moisture. It was then cooled in an ice-bath, stirred and treated with 200 ml of 20% aqueous sodium hydroxide which was added dropwise until foaming subsided and subsequently in one lot. The mixture was diluted with 200 ml of water and 100 ml of benzene, and the benzene layer was separated. The aqueous layer was extracted thrice with ether, and the combined benzene and ether extracts were washed with water, dried over anhydrous magnesium sulfate and stripped of the solvents under reduced pressure. The residue was dissolved in the requisite quantity of anhydrous ether, and the solution was added to an excess of anhydrous ether saturated with gaseous hydrogen chloride. The solid that separated was filtered off, washed with anhydrous ether and recrystallized from tetrahydrofuran to yield the title compound as the hemihydrate, m.p. 173°–175° (melts to an opaque fluid).

The compounds listed below can be prepared by a similar procedure:

(±)7-(or: -8-)fluoro-1,2,3,4,4a,5,10,10a-octahydro-2-methyl-5,10-o-benzenobenz[g]isoquinoline hydrochloride, m.p. 85°–115° (dec.)

(±)7-(or: -8-)chloro-1,2,3,4,4a,5,10,10a-octahydro-2-methyl-5,10-o-benzenobenz[g]isoquinoline hydrochloride hemihydrate, m.p. 50°–60° (dec.)

EXAMPLE 3

(±)1,2,3,4,4a,5,10,10a-Octahydro-5,10-o-benzenobenz[g]isoquinoline Hydrochloride A mixture of 8.5 g (±)1,2,3,4,4a,5,10,10a-octahydro-5,10-o-benzenobenz[g]isoquinoline-2-carboxylic ethyl ester, 20 g of powdered potassium hydroxide and 100 ml of 1-butanol was refluxed for 3 hours and then stripped of the solvent under reduced pressure. The residue was taken up in 200 ml of cold water and extracted twice with chloroform. The combined chloroform extracts were washed with water, dried over anhydrous magnesium sulfate and stripped of the solvent under reduced pressure. The residue was dissolved in the requisite quantity of anhydrous ether, and the solution added to an excess of anhydrous ether saturated with hydrogen chloride. The product was filtered off and recrystallized from a mixture of methanal and anhydrous ether to yield the title compound, m.p. 339°–340° (dec.).

The compounds listed below can be prepared by a similar procedure:

(±)7-(or: -8-)-fluoro-1,2,3,4,4a,5,10,10a-octahydro-5,10-o-benzenobenz[g]isoquinoline hydrochloride, m.p. 315°–317° (dec.)

(±)7-(or: -8-)-chloro-1,2,3,4,4a,5,10,10a-octahydro-5,10-o-benzenobenz[g]isoquinoline hydrochloride, 302°–304° (dec.)

(±)6-(or: -9-)chloro-1,2,3,4,4a,10,10a-octahydro-5,10-o-benzenobenz[g]isoquinoline hydrochloride, 294°–296° (dec.)

(±)1,2,3,4,4a,5,10,10a-octahydro-5-(or: -10)-methyl-5,10-o-benzobenz[g]isoquinoline hydrochloride, m.p. 311°–314° (dec.)

(±)1,2,3,4,4a,5,10,10a-octahydro-7-(or: -8-)methyl-5,10-o-benzenobenz[g]isoquinoline hydrochloride, m.p. 238°–239° (dec.)

(±)6-(or: -9-)-chloro-1,2,3,4,4a,5,10,10a-octahydro-2-methyl-5,10-o-benzenobenz[g]isoquinoline hydrochloride, m.p. 294°–296°

(±)6,10-dichloro-1,2,3,4,4a,5,10,10a-octahydro-2-methyl-5,10-o-benzenobenz[g]isoquinoline hydrochloride, m.p. 263°–264° (dec.) (sinters at 120°)

(±)1,2,3,4,4a,-5,10,10a-octahydro-2,5-dimethyl-5,10-o-benzenobenz[g]isoquinoline or (±)1,2,3,4,4a,5,10,-10a-octahydro-2,10-dimethyl-5,10-o-benzenobenz[g]isoquinoline, m.p. 104°–106°.

EXAMPLE 4

(±)1,2,3,4,4a,5,10,10a-Octahydro-2-phenoxyacetyl-5,10-o-benzenobenz[g]isoquinoline A solution of phenoxyacetyl chloride (7.48 g) in chloroform (25 ml) was added dropwise to a vigorously stirred mixture of a solution of (±)1,2,3,4,4a,5,10,10a-octahydro-5,10-o-benzenobenz[g]isoquinoline (8.8 g) in chloroform (150 ml) and a saturated aqueous solution of sodium carbonate (150 ml) at room temperature. After the addition was complete, the mixture was stirred for 30 minutes at room temperature. The chloroform layer was then separated, washed successively with water, 3 N hydrochloric acid and water, dried over anhydrous magnesium sulfate and stripped of the solvent under reduced pressure. The residual viscous liquid, on trituration with hexane-ether and cooling, furnished a solid which was recrystallized from a mixture of benzene and hexane to yield the title compound, m.p. 165°–167°.

The compounds listed below can be prepared by a similar procedure:

(±)1,2,3,4,4a,5,10,10a-octahydro-2-diphenylacetyl-5,10-o-benzenobenz[g]isoquinoline, m.p. 165°–168°

(±)2-(adamantyl-1-methyl)-1,2,3,4,4a,5,10,10a-octahydro-5,10-o-benzenobenz[g]isoquinoline (±)1,2,3,4,4a,5,10,10a-octahydro-2-phenylacetyl-5,10-o-benzenobenz[g]isoquinoline, viscous liquid.

EXAMPLE 5

(±)1,2,3,4,4a,5,10,10a-Octahydro-2-[2-(phenoxy)ethyl]-5,10-o-benzenobenz[g]isoquinoline A one molar solution of borane in tetrahydrofuran (100 ml) was added slowly to a stirred solution of (±)1,2,3,4,4a,5,10,10a-octahydro-2-phenoxyacetyl-5,10-o-benzenobenz[g]isoquinoline (7.8 g) in anhydrous tetrahydrofuran (200 ml) in a nitrogen atmosphere. After the addition was complete, the mixture was stirred and refluxed in a nitrogen atmosphere for 3 hours and cooled to room temperature. The excess borane was decomposed by dropwise addition of 6 N hydrochloric acid. The mixture was then evaporated to dryness under reduced pressure and the residue was refluxed with a mixture of 80 ml of 6 N hydrochloric acid and 20 ml of acetic acid for 1 hour. The mixture was evaporated to dryness and the residue was treated with an excess of 10% aqueous sodium hydroxide and extracted twice with chloroform. The combined chloroform extracts were washed with water, dried over anhydrous magnesium sulfate and stripped of the solvent under reduced pressure. The residual liquid solidified on trituration with ether, and the solid was filtered off and recrystallized from ethanol to yield the title compound, m.p. 115°–117°.

The compounds listed below can be prepared by a similar procedure:

(±)1,2,3,4,4a,5,10,10a-octahydro-2-(2,2-diphenylethyl)-5,10-o-benzenobenz[g]isoquinoline hydrochloride, m.p. 250°–252° (dec.)

(±)2-(1-adamantylmethyl)-1,2,3,4,4a,5,10,10a-octahydro-5,10-o-benzenobenz[g]isoquinoline, hydrochloride hemihydrate, m.p. 190°–192°

(±)1,2,3,4,4a,5,10,10a-octahydro-2-phenethyl-5,10-o-benzenobenz[g]isoquinoline, hydrochloride hemihydrate, m.p. 150°–152°

EXAMPLE 6

(±)4-(1,2,3,4,4a,5,10,10a-Octahydro-5,10-o-benzenobenz[g]isoquinoline-2-yl)-2-butanone Maleate A mixture of (±)1,2,3,4,4a,5,10,10a-octahydro-5,10-o-benzenobenz[g]isoquinoline (11.0 g), methyl vinyl ketone (3.5 g) and ethanol (150 ml) was stirred and refluxed for 2 hours and then stripped of the solvent under reduced pressure. The residual viscous liquid was dissolved in requisite quantity of anhydrous ether and the solution was added to a solution of 6.0 g of maleic acid in ether. The sticky solid that separated was removed by decantation, triturated with 2-propanol, filtered and recrystallized from ethanol containing a little methanol to yield the title compound, m.p. 149°–151° (dec.)

If ethyl acrylate were used in the place of methyl vinyl ketone in the above reaction, (±)1,2,3,4,4a,5,10,10a-octahydro-5,10-o-benzenobenz[g]isoquinoline-2-propionic acid ethyl ester, m.p. 80°–82° would be obtained.

EXAMPLE 7

(±)4-(1,2,3,4,4a,5,10,10a-Octahydro-5,10-o-benzenobenz[g]isoquinoline-2-yl)-2-butanol Hydrochloride Powdered sodium borohydride (2.0 g) was added in small portions to a stirred solution-suspension of (±)4-(1,2,3,4,4a,5,10,10a-octahydro-5,10-o-benzenobenz[g]isoquinoline-2-yl)-2-butanone maleate (9.0 gms) in ethanol (100 ml). After the addition was complete, the mixture was stirred and refluxed for 1 hour and then stripped of the solvent under reduced pressure. The residue was treated with 100 ml of 1 N aqueous sodium hydroxide and the mixture was extracted twice with chloroform. The combined chloroform extracts were washed with water, dried over magnesium sulfate and stripped of the solvent, under reduced pressure. The residual viscous liquid was dissolved in requisite quantity of ether and the solution was added to an excess of ether saturated with gaseous hydrogen chloride. The product was filtered off and recrystallized from tetrahydrofuran to yield the title product, m.p. 215°–218° (dec.).

EXAMPLE 8

(±)1,2,3,4,4a,5,10,10a-Octahydro-5,10-o-benzenobenz[g]isoquinoline-2-propionic Acid Hydrochloride A mixture of 7.2 g of (±)1,2,3,4,4a,5,10,10a-octahydro-5,10-o-benzenobenz[g]isoquinoline-2-propionic ester, 75 ml dioxane and 100 ml of 4 N hydrochloric acid was stirred and refluxed for 4 hours and then evaporated to dryness under reduced pressure. The residue was triturated with ether, filtered and recrystallized from a mixture of 2-propanol and ether to yield the title compound, m.p. 160°–165°.

EXAMPLE 9

(±)2-(1-butyl)-1,2,3,4,4a,5,10,10a-Octahydro-5,10-o-benzenobenz[g]isoquinoline Maleate A mixture of (±)1,2,3,4,4a,5,10,10a-octahydro-5,10-o-benzenobenz[g]isoquinoline (6.5 g), 1-bromobutane (3.4 g), potassium iodide (4.7 g), anhydrous potassium carbonate (5.0 g) and dimethyl formamide (75 ml) was stirred and heated in a steam bath for 6 hours and then stripped of most of the solvent under reduced pressure. The residue was taken up in ether, filtered and the filtrate added to an excess of anhydrous ethers saturated with hydrogen chloride. The sticky hydrochloride that separated was separated by decantation, dissolved in 50 ml of water, basified with 10% aqueous sodium hydroxide and the mixture extracted with ether. The ether extract was washed with water, dried over magnesium sulfate and stripped of the solvent under reduced pressure to yield a viscous liquid which was dissolved in a small quantity of anhydrous ether. The resulting solution was added to a solution of maleic acid (2 g) in anhydrous ether (150 ml). The sticky maleate that separated was removed by decantation, dissolved and cooled to yield the title compound, m.p. 182°–183° (dec.).

DOSAGE FORMS

The antidepressive agents of this invention can be administered as treatment for pyschiatric depression of the reactive and endogenous types in mammals by any means that produces contact of the active agent with the agent's site of action in the body of a mammal. They can be administered by any conventional means available for use in conjunction with pharmaceuticals, either as individual therapeutic agents or in a combination of therapeutic agents. They can be administered alone, but are generally administered with a pharmaceutical carrier selected on the basis of the chosen route of administration and standard pharmaceutical practice.

The dosage administered will, of course, vary depending upon known factors such as the pharmacodynamic characteristics of the particular agent, and its mode and route of administration; age, health and weight of the recipient; nature and extent of symptoms, kind of concurrent treatment, frequency of treatment, and the effect desired. Usually a daily oral dosage of active ingredient can be about 0.01 to 50 milligrams per kilogram of body weight. Ordinarily, when the more potent compounds of this invention are used, a dosage of 0.03 to 15 and preferably 0.1 to 3 milligrams per kilogram per day, given in divided doses 2 to 4 times a day or in sustained release form, is effective to obtain desired results. It can also be administered parenterally, in sterile liquid forms.

Dosage forms (compositions) suitable for internal administration contain from about 1.0 milligram to about 500 milligrams of active ingredient per unit. In these pharmaceutical compositions the active ingredient will ordinarily be present in an amount of about 0.5-95% by weight based on the total weight of the composition.

The active ingredient can be administered orally in solid dosage forms, such as capsules, tablets and powders, or in liquid dosage forms, such as elixirs, syrups and suspensions; it can also be administered parenterally, in sterile liquid dosage forms.

Gelatin capsules contain the active ingredient and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coating for selective disintegration of the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration contain preferably a water soluble salt of the active ingredient, suitable stabilizing agents, and if necessary, buffer substances. Antioxidizing agents such as sodium bisulfite, sodium sulfite, or ascorbic acid either alone or combined are suitable stabilizing agents. Also used are citric acid and its salts and sodium EDTA. In addition parenteral solutions can contain preservatives, such as benzalkonium chloride, methyl- or propylparaben and chlorobutanol.

Suitable pharmaceutical carriers are described in Remington's Pharmaceutical Sciences, E. W. Martin, a standard reference text in this field.

Useful pharmaceutical dosage forms for administration of the compounds of this invention can be illustrated as follows:

CAPSULES

A large number of unit capsules are prepared by filling standard two-piece hard gelatin capsules each with 50 milligrams of powdered active ingredient, 175 milligrams of lactose, 24 milligrams of talc and 6 milligrams magnesium stearate.

A mixture of active ingredient in soybean oil is prepared and injected by means of a positive displacement pump into gelatin to form soft gelatin capsules containing 50 milligrams of the active ingredient. The capsules are washed in petroleum ether and dried.

TABLETS

A large number of tablets are prepared by conventional procedures so that the dosage unit is 50 milligrams of active ingredient, 0.2 milligrams of colloidal silicon dioxide, 5 milligrams of magnesium stearate, 275 milligrams of microcrystalline cellulose, 11 milligrams of cornstarch and 98.8 milligrams of lactose. Appropriate coatings may be applied to increase palatability or delay absorption.

INJECTABLE

A parenteral composition suitable for administration by injection is prepared by stirring 1.5% by weight of active ingredient in 10% by volume propylene glycol and water. The solution is made isotonic with sodium chloride and sterilized.

SUSPENSION

An aqueous suspension is prepared for oral administration so that each 5 milliliters contain 50 milligrams of finely divided active ingredient, 200 milligrams of sodium carboxymethyl cellulose, 5 milligrams of sodium benzoate, 1.0 grams of sorbitol solution, and 0.025 milliliters of vanillin.

UTILITY

The antidepressant activity of the compounds of this invention is evidenced by tests conducted in female white mice in which prevention of tetrabenazine-induced sedation and depression is demonstrated. This mouse test is predictive of human antidepressant response (Everett, "The Dopa Response Potentiation Test and Its Use in Screening for Antidepressant Drugs," pp 164 in "Antidepressant Drugs" (Proceedings of the First International Symposium), S. Garattini and M. N. G. Dukes, eds., 1967).

TEST PROCEDURE

Groups of 10 Carworth $CF_1S$ female mice, 18–21 g each, were fasted 1.5 hours and were intubated with antagonist compounds at oral doses of 0, 0.33, 1, 3, 9, 27 and 81 mg/kg in 0.20 ml of 1% methocel-1.25% Tween 80. The mice were challenged 30 minutes later with tetrabenazine (as the methanesulfonate), 32 mg/kg intraperitoneally (dissolved in 0.20 ml 0.05 M KCl at pH 2.0). One hour after antagonist (30 minutes after tetrabenazine), the mice were examined for signs of exploratory activity and ptosis (eyelid closure). Normal exploratory activity (relief from sedation) was recorded when a mouse lifted by the tail from a group of 10 in a testing box and placed on a stainless steel testing box lid (12.5"×8" with 0.33" mesh) either turned its head horizontally 30° in both directions or moved to the edge of the screen within 10 seconds after being placed on the screen. Relief from ptosis was recorded when exactly two seconds after placing the mouse facing the observer, lid closure was less than 50% in both eyes. Table 1 lists the ED50's (the effective dose at which fifty percent of the mice exhibit a given symptom) for compounds of the invention and for a standard antidepressant, amitriptyline.

TABLE 1

| R | $R_1$ | $R_2$ | $R_3$ | $R_4$ | ANTAGONISM OF TETRABENAZINE INDUCED DEPRESSION IN MICE ORALLY AT 1 HR POST DRUG ED50 (mg/kg) FOR PREVENTION OF | |
|---|---|---|---|---|---|---|
| | | | | | PTOSIS | EXPLORATORY LOSS |
| —H | H | H | H | H | .41 | 1.5 |
| —$CH_3$ | H | H | H | H | 1.0 | 6.0 |
| —$CH_2CH_2COCH_3$ | H | H | H | H | 2.1 | 4.4 |
| —$CH_2CH_2$—CH(OH)—$CH_3$ | H | H | H | H | 4.9 | 5.6 |
| —$COOC_2H_5$ | H | H | H | H | 2.1 | 5.4 |
| —$CH_2CH_2COOC_2H_5$ | H | H | H | H | 8.1 | 20 |
| —$CH_2CH_2C_6H_5$ | H | H | H | H | 11.8 | 13.6 |
| —$CH_2CH_2COOH$ | H | H | H | H | 15 | 27 |
| —$CH_2CH_2$—O—$C_6H_5$ | H | H | H | H | 10.8 | 27 |
| —$CH_2CH_2CH_2CH_3$ | H | H | H | H | 11.2 | 19 |
| —$CH_2CH(C_6H_5)_2$ | H | H | H | H | 12 | 47 |
| 1-adamantyl | H | H | H | H | 24 | 41 |
| —H | H | H | 7 or 8-F | H | .58 | 1.7 |
| —$CH_3$ | H | H | 6 or 9-Cl | H | 1.3 | 1.4 |
| —H | H | H | 7 or 8-Cl | H | 1.4 | 1.7 |
| —$CH_3$ | H | H | 7 or 8-F | H | 2.0 | 2.7 |
| —H | H | H | 6 or 9-Cl | H | 2.2 | 2.5 |
| —$CH_3$ | H | H | 7 or 8-Cl | H | 3.4 | 4.5 |
| —H | H | H | 6-Cl | 10-Cl | 9.0 | 12 |
| —$CH_3$ | H | H | 6-Cl | 10-Cl | 12.2 | 22 |
| —$CH_3$ | $CH_3$(H) | H($CH_3$) | H | H | 21 | 27 |
| —H | $CH_3$(H) | H($CH_3$) | H | H | 22 | 38 |
| —H | H | H | 7 or 8-$CH_3$ | H | .94 | 4.8 |
| Amitriptyline | | | | | 1.0 | 1.2 |

What is claimed is:

1. A compound of the formula

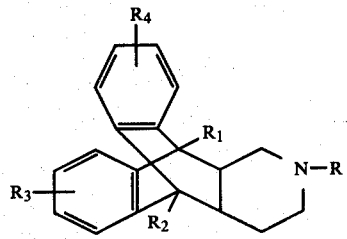

where
R is H; $C_1$-$C_6$ alkyl, optionally substituted with —$OR_5$, phenyl or 1-adamantyl;

—$(CH_2)_n\overset{O}{\overset{\|}{C}}R_6$;  —$(CH_2)_m\overset{O}{\overset{\|}{C}}OR_7$;

or 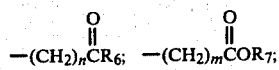

$R_1$ and $R_2$ are both H, or, when R=H or $CH_3$, then one of $R_1$ and $R_2$ may be $CH_3$;
$R_3$ and $R_4$ are independently H, Cl, F or $CH_3$;
$R_5$ is H, $CH_3$ or phenyl;
$R_6$ is $C_1$-$C_3$ alkyl;
$R_7$ is H or $C_1$-$C_4$ alkyl;
n is 1, 2, 3 or 4; and
m is 0, 1, 2, 3 or 4;
provided that, when m=0, then $R_7$ is other than H; and pharmaceutically suitable acid and base salts thereof.

2. A compound of claim 1 wherein R is H, $CH_3$ or $CO_2CH_2CH_3$.

3. A compound of claim 1 where $R_1$ and $R_2$ are H.

4. A compound of claim 1 where $R_3$ and $R_4$ are H or mono-F.

5. A compound of claim 1 wherein R, $R_3$ and $R_4$ are H.

6. A compound of claim 1 wherein R, $R_1$, $R_2$, $R_3$ and $R_4$ are H.

7. The compound of claim 1 which is (±)1,2,3,4,4a,5,10,10a-octahydro-5,10-o-benzenobenz[g]isoquinoline hydrochloride.

8. The compound of claim 1 which is (±)7-fluoro-1,2,3,4,4a,5,10,10a-octahydro-5,10-o-benzenobenz[g]isoquinoline hydrochloride.

9. The compound of claim 1 which is (±)8-fluoro-1,2,3,4,4a,5,10,10a-octahydro-5,10-o-benzenobenz[g]isoquinoline hydrochloride.

10. The compound of claim 1 which is (±)1,2,3,4,4a,5,10,10a-octahydro-5,10,o-benzenobenz[g]isoquinoline-2-carboxylic acid ethyl ester.

11. A pharmaceutical composition consisting essentially of a suitable pharmaceutical carrier and an effective antidepressive amount of a compound of any one of claims 1 to 10.

12. A method alleviating depression in mammals comprising administering to the mammal an antidepressive amount of a compound of any one of claims 1 to 10.

* * * * *